United States Patent [19]
Fanget et al.

[11] Patent Number: 6,149,917
[45] Date of Patent: Nov. 21, 2000

[54] INDUSTRIAL PRODUCTION PROCESS FOR A VACCINE AGAINST JAPANESE ENCEPHALITIS VIRUS AND VACCINE PRODUCED

[75] Inventors: Bernard Fanget, sur l'Arbresle; Alain Francon, Bessenay; Pierre Heimendinger, Lyons, all of France

[73] Assignee: Pasteur Merieux Serums et Vaccins, Lyon Cedex, France

[21] Appl. No.: 09/000,263

[22] PCT Filed: Jul. 29, 1996

[86] PCT No.: PCT/FR96/01195

§ 371 Date: Aug. 13, 1998

§ 102(e) Date: Aug. 13, 1998

[87] PCT Pub. No.: WO97/04803

PCT Pub. Date: Feb. 13, 1997

[30] Foreign Application Priority Data

Aug. 1, 1995 [FR] France .................................. 95 09374
Mar. 22, 1996 [FR] France .................................. 96 03638

[51] Int. Cl.$^7$ .............................. A61K 39/12; C12N 7/02
[52] U.S. Cl. ......................................... 424/218.1; 435/239
[58] Field of Search .......................... 424/218.1; 435/239

[56] References Cited

U.S. PATENT DOCUMENTS 4,725,546 2/1988 Sakamoto et al. ...................... 435/239

FOREIGN PATENT DOCUMENTS 0 171 735   2/1986   European Pat. Off. .
WO 91/09935 7/1991   WIPO .

OTHER PUBLICATIONS

Venkateshan et al., (1977) "Comparative Studies of Different Methods For Concentration of Japanese Encephalitis Virus Antigens Prepared From Vero Cell Culture." *Biological Abstracts*, vol. 64, pp. 245. Abstract No. 2449.

*Primary Examiner*—Terry McKelvey
*Attorney, Agent, or Firm*—McDonnell Boehnen Hulbert & Berghoff

[57] ABSTRACT

A method is disclosed for industrially producing a Japanese encephalitis vaccine, wherein (a) cells from a cell line are cultured, (b) the resulting cell culture is inoculated with a Japanese encephalitis virus in the presence of a viral growth medium, (c) the virus is propagated and multiplied on the cells, (d) the viral growth medium is recovered in the form of a suspension of viruses produced by the cells, (e) the virus suspension is purified in at least one ion exchange chromatography step and a gel permeation step, and (f) the virus suspension is formulated and converted into a pharmaceutical form to preserve it until the moment of use. A Japanese encephalitis vaccine characterised in that it comprises a Japanese encephalitis virus produced by culturing cells from a cell line, and in that the cellular DNA content is less than 100 pg/dose, is also disclosed.

10 Claims, No Drawings

INDUSTRIAL PRODUCTION PROCESS FOR A VACCINE AGAINST JAPANESE ENCEPHALITIS VIRUS AND VACCINE PRODUCED

This is a National Stage of International Application No. PCT/FR96/01195, filed Jul. 29, 1996.

The present invention relates to a process for the production of a vaccine for the prevention of Japanese encephalitis, based on Japanese encephalitis virus (JEV) and in particular on a vaccine which can be used in man. The invention also relates to a vaccine obtained by this process.

Japanese encephalitis virus, whose transmission vector is a mosquito, is the cause of serious infections, known as Japanese encephalitides, in many Far Eastern countries and in other areas of the world.

Vaccines against Japanese encephalitis are known, these being obtained by processes which consist in injecting JEV intracranially into baby mice and in harvesting the infected tissues. The tissue emulsion obtained is then purified, generally by precipitation methods, in particular with protamine. Other techniques for purification of these tissue preparations have also been proposed in the literature, such as techniques of ultrafiltration, of filtration and centrifugation, or of precipitation with polyethylene glycol, it being possible for these techniques to be combined with each other or with techniques of gel filtration or of chromatography on cellulose sulphate or on crosslinked polysaccharide sulphate (JP-B-65,000,611, JP-A-53,133,627, JP-A-50,048,118, JP-A-2,223,531, U.S. Pat. No. 4,725,546, JP-A-49,020,322 and B-81,005,204, JP-B-67,025,408)

In the prior art, the viral preparations are inactivated, as recommended by the World Health Organization, by chemical agents such as formaldehyde according to standardized procedures, namely long-term inactivation for 50 to 60 days at +4° C. at a formaldehyde concentration of 1/2000, on account of the instability of the viruses at higher temperatures in this environment.

The commercial vaccines thus obtained are effective but are difficult and expensive to prepare, to purify and to inactivate. They may moreover lead to side reactions due to contaminants originating from the baby mouse tissues, thereby occasionally limiting their application.

It is thus desirable to be able to produce a vaccine by other more industrial techniques and in particular by using a multiplication and a propagation of the virus on a cell line. However, the production of a vaccine in large quantities, using highly industrialized methods, is much more difficult than in the case of intracranial multiplication, not only on account of the considerable quantities which must be dealt with, but also on account of the difficulties in obtaining and controlling high yields and also on account of the purification problems posed by contaminants which are then encountered and which may originate from the cells or from the viral multiplication medium.

It is known in the prior art that Japanese encephalitis virus can propagate on various cell cultures, including cultures of cell lines, in particular Vero cells. However, the culturing methods disclosed do not make it possible to obtain satisfactory yields under large-scale industrial culturing conditions, the only conditions allowing production at moderate cost. Nor does the prior art describe any methods for purifying to a high degree the viral preparations originating from propagation and multiplication on cell lines.

The invention thus proposes to overcome these drawbacks and to provide a process for the production of a vaccine against Japanese encephalitis, which process may be used on a large scale and under safe, rapid and economic conditions and makes it possible to obtain an effective vaccine of very high purity in a very good industrial yield.

In order to achieve these aims, the subject of the invention is a process for the industrial production of a vaccine against Japanese encephalitis, characterized in that it comprises the following steps:

a) culturing of cells originating from a cell line, b) inoculation of the cell culture obtained by Japanese encephalitis virus in the presence of a viral multiplication medium, c) propagation and multiplication of the virus on the cells, d) harvesting of the viral multiplication medium constituting a suspension of viruses produced by the cells, e) purification of the viral suspension by at least one ion-exchange chromatographic step and a gel permeation step, f) formulation and incorporation of the viral suspension in a pharmaceutical form in order to ensure its conservation up to the time of its use.

According to a particular feature of the invention, the amount of virus inoculated corresponds to a multiplicity of infection of less than 0.1. Thus, a good yield is obtained for the viral multiplication and propagation.

According to a particular feature of the invention, the process also comprises a step of inactivation of the viral suspension before or after the purification step e). It is thus possible to manufacture an inactivated vaccine while at the same time using a virulent strain for the viral multiplication and propagation.

According to a feature of the process of the invention, the inactivation is performed using a chemical agent at room temperature. The inactivation thus takes place rapidly.

According to a particular embodiment, the process consists in using a Vero cell line in order to ensure the viral multiplication. It is thus possible to obtain good yields since these cells are very permissive to Japanese encephalitis virus.

According to another embodiment feature of the invention, the process consists in purifying the viral suspension by carrying out the following steps:

ion-exchange chromatography, adsorption chromatography, gel permeation.

It is thus possible to obtain a vaccine with a very high degree of purity.

According to another embodiment of the invention, the process also consists, after the harvesting step d), in reintroducing new viral multiplication medium, in waiting for a sufficient period to allow further multiplication of the virus and in carrying out a further harvesting of the viral multiplication medium.

It is thus possible to obtain a considerable number of harvests from the same cell culture.

The subject of the invention is also a vaccine obtained by culturing on cells originating from a cell line, characterized in that it includes Japanese encephalitis virus and in that the cellular DNA content is less than 100 pg/dose.

Such a vaccine has both the efficacy and the safety necessary, both from the point of view of the viral contaminants and of the proteins, to be administered systematically to anybody liable to be in contact with the virus.

Other subjects and advantages of the present invention will emerge on reading the description which follows.

According to the invention, the cell culture may be prepared either in a fermenter or traditionally in flasks (Roux dishes, rolling flasks, Multitray™, Cell-Cube™, etc.).

Preferably, however, a large-volume fermenter (500 to 2000 l) containing microcarriers is used along with a cell culture medium, into which an inoculum of cells from a cell line permissive to Japanese encephalitis virus is introduced; this cell line may in particular be BHK21 (Baby Hamster Kidney) cells or alternatively Vero cells.

The microcarriers allowing the culturing in suspension in the fermenter may be various microcarriers already known for such a use; mention may be made in particular of Cytodex 1™ particles at a concentration of 1 to 3 g/l of culture medium as being particularly suitable for culturing Vero cells. The durations, temperatures and other culturing conditions, and in particular the composition of the culturing medium, are adapted as a function of the nature of the Vero cells on Cytodex 1™ microcarriers, a duration of 4 days was suitable in order to obtain good cell growth and thus make it possible to inoculate the virus before the stationary phase of the culture. The culture medium is then replaced by a viral multiplication medium and an inoculum of Japanese encephalitis virus is introduced into the fermenter in an amount calculated to have a low value for the multiplicity of infection (or MOI), which is the ratio of the amount of viral particles introduced to the number of cells present.

This multiplicity is preferably less than about 0.1 and more preferably less than 0.01.

The viral strain used may be an attenuated strain such as the strain SA 14-14-2 or any known virulent immunogenic strain, such as the Nakayama or Beijing strain. The strain $P_3$ at the 88th passage supplied by the NVSI (National Vaccine and Serum Institute, Beijing) is well suited to the needs of the invention.

The medium used for the viral multiplication is a usual medium, such as MEM, in which it is important that the amount of proteins is reduced as much as possible. A medium whose concentration of proteins, usually human albumin, is less than 5 g/l is preferably used. Equally preferably, a culture medium completely lacking proteins is used.

The period required for viral multiplication and propagation may be determined by monitoring the infectious titre. Harvesting of viruses is considered possible when the LD 50/ml titre is about $10^7$ or $10^8$. The harvesting is carried out by simple removal of the viral multiplication medium which contains the viruses produced by the cells. Advantageously, after having removed the viral multiplication medium, new medium is reintroduced into the fermenter so as to allow a further viral multiplication leading to a further harvest. It is thus readily possible to obtain up to 8 successive harvests in the same fermenter from the same cell culture. The period required for propagation and multiplication of the virus in order to obtain an LD 50/ml assay of $10^7$ or $10^8$ is generally from 2 to 3 days; a first harvest is preferably performed 3 days after the viral inoculation, followed by successive harvests every 2 or 3 days.

Thus, a complete cycle in a fermenter may last for 23 days divided up as follows:

D0: commencement of the culturing of cells on the microsupports in the fermenter,
D4: replacement of the cell culture medium by viral multiplication medium and inoculation of the virus,
D7: first harvest,
D9: second harvest,
D11: third harvest,
D14: fourth harvest,
D16: fifth harvest,
D18: sixth harvest,
D21: seventh harvest,
D23: eighth harvest.

The various harvests obtained may then be processed separately or as a mixture.

The processing consists either of a purification alone or of a purification and an inactivation, it being possible for the inactivation to be performed before or after the purification step.

The inactivation is an essential step in the process according to the invention when the viral strain used at the start is a virulent strain; on the other hand, when the strain used for the viral multiplication is an attenuated strain such as the strain SA 14-14-2, this inactivation step may either be omitted or performed so as to be under the safest possible conditions.

According to the invention, the inactivation is carried out using chemical agents at room temperature. According to the invention, room temperature refers to a temperature considerably higher than +4° C. which is the temperature usually used by inactivation of JEV. This temperature may advantageously be between 20 and 37° C. and a temperature of about 25° C. is preferred. Indeed, it has been observed that the virus is rapidly inactivated at this temperature and it has moreover been possible to note that, surprisingly, the virus contained in its viral multiplication medium is stable despite the high temperature; this very short duration of the inactivation is an important advantage of the process of the invention from an industrial point of view.

The chemical agents used for the inactivation may in particular be formaldehyde or β-propiolactone; formaldehyde is preferred. The inactivation may be carried out, for example, using formaldehyde at 25 or at 37° C. for 14 days or less; the duration will preferably be at least 7 days. Advantageously, according to the invention, the formaldehyde concentration used may be less than that used conventionally in the inactivation of JEV; it may, for example, be from about 1/2000 to 1/8000 and in particular 1/4000.

It is also possible to carry out 2 successive and different inactivation steps using, for example, 2 different chemical agents.

It is also possible, before this inactivation step, to filter each harvest so as to remove cell debris (proteins, nucleic acids, etc.), as well as to concentrate each one so as to increase the viral titre and the protein content of the liquid medium. The concentration factor is preferably at least equal to 10, for example about 1000. Concentrating may be carried out by the usual means and in particular by ultrafiltration.

The viral suspension, which may or may not be inactivated depending on the process used, must be purified. According to an important feature of the invention, the purification step comprises at least one chromatography step. Advantageously, the following 3 steps are carried out successively:

ion-exchange chromatography
adsorption chromatography
gel permeation.

The ion-exchange chromatography is preferably a chromatographic exchange of anions, whether weak or strong ones. The support used is, for example, DEAE-Spherodex™ (sold by Biosepra, USA) which selectively retains the viral particles and allows the bulk of the contaminant proteins to pass through.

The eluate containing the viruses may then be carried out on supports such as hydroxyapatite or chelating gels (calcium-chelating, etc.). In this case, the virus does not become bound to the support, which more especially retains the nucleic acids.

After this step, gel filtration or molecular sieving (again called gel permeation) is carried out on any suitable support such as Sepharose 6FF™ (Pharmacia) or Fractogel™ (E.Merck). During this operation, elution makes it possible to recover the viral particles in the first fraction; the following elution peaks correspond to the viral proteins and to the residual impurities. Thus, for the manufacture of a vaccine, the first fraction only of the eluate is conserved.

Advantageously, between the adsorption chromatography and the gel filtration, a step of concentrating may be carried out, preferably by ultrafiltration with a membrane whose cut-off threshold is 10,000 daltons.

The purified and optionally inactivated viral suspension is then formulated in order to obtain the desired antigenic titre; it is also possible to add a stabilizer or an adjuvant thereto; it is subsequently made into a pharmaceutical form so as to be conserved under good conditions until the time of its use.

EXAMPLE

1. Materials

Vero Cells: the Vero cells used to inoculate the fermenter are derived from a Vero cell bank at the 137th passage, this bank having undergone all the checks necessary for its characterization and qualification.

The JEV: the viral strain used is the strain $P_3$ at the 88th passage supplied by the NVSI.

A received vial of virus is suspended in 100 ml of medium and filtered using a 0.1 $\mu$m filter. The solution is used to infect two 75 cm² flasks. Five days later, the supernatant collected is filtered (0.2 $\mu$m filter). Several harvests were made and the mixture forming the primary seeding batch has an LD 50/ml titre $=10^{8.16}$. The working seeding batch is prepared in a proportion of 10 ml of primary seeding batch to infect 12 850 cm² rolling flasks. Several harvests may be taken and the mixture of 30.2 liters has an LD 50/ml titre$=10^{8.31}$.

The primary and working seeding batches are subsequently checked so as to ensure their characterization and qualification.

2. Culturing process

The 500 l fermenter tank is filled with a conventional culture medium for Vero cells containing Cytodex 1™ microcarriers at a concentration of 3 g/l. The medium is seeded with an inoculum of Vero cells (200,000 cells/ml).

The cells are left to attach and to grow for four days. At the end of the four days, the culture medium is replaced by a viral multiplication medium.

A viral inoculum is introduced into the tank with an amount of virus calculated so as to have a multiplicity of infection MOI equal to 1/500. The various cultures are prepared at a temperature of 37° C. Three days after the viral inoculation, the viral multiplication medium is collected, this giving the first harvest. The viral multiplication medium is replaced by a new medium and further harvesting is carried out every other day, the total number of harvests being equal to six.

Table I shows the titres obtained at each harvest.

TABLE I

| Harvest No. | H1 | H2 | H3 | H4 | H5 | H6 |
| --- | --- | --- | --- | --- | --- | --- |
| Days after infection | 3 | 5 | 7 | 10 | 12 | 14 |

TABLE I-continued

| Harvest No. | H1 | H2 | H3 | H4 | H5 | H6 |
| --- | --- | --- | --- | --- | --- | --- |
| Titre LD 50/ml | $10^{8.4}$ | $10^{8.4}$ | $10^{8.5}$ | $10^{8.1}$ | $10^{8.2}$ | $10^{7.3}$ |

The harvests are filtered on a membrane filter (pore diameter: 0.2 $\mu$m).

The harvests are all mixed together.

The harvest mixture is concentrated by a factor of 100 by ultrafiltration on a 10,000 dalton membrane.

A formaldehyde solution at a final concentration of 1/4000 is added to the concentrated harvest mixture and the resulting mixture is maintained at room temperature (from 20 to 25° C.) with continuous stirring for 14 days.

A further filtration is then carried out and the inactivation is verified by a two-step check according to the WHO procedure (Technical Report 771 from 1988).

All the preparations inactivated with formaldehyde proved to be satisfactory.

The inactivated solution is passed through an ion-exchange chromatography column containing DEAE groups equilibrated at pH 8 (DEAE-Spherodex™ resin). The virus is retained on the column. After washing with a phosphate buffer, the virus is eluted with a phosphate buffer, 0.2 M NaCl. Most of the protein contaminants are thus removed.

The eluate is purified by chelation affinity by calcium interaction, by injecting the eluate through a Chelating Sepharose™ column (Pharmacia). The virus is not bound and travels directly through the column.

Concentrating is then carried out by ultrafiltration on membranes whose cut-off threshold is 10,000 Da, in order to reduce the volume of the viral suspension by a factor of about 20.

The concentrated solution of pre-purified virus is introduced onto a Sepharose 6FF™ column. An elution is carried out with a 0.2 M NaCl phosphate buffer. The viral particles are eluted in the excluded fraction.

The characteristics of the purification process are featured in Table II.

TABLE II

| Step | DEAE | Chelation | Gel filtration |
| --- | --- | --- | --- |
| Residual proteins (*) | 50% | 100% | 0.4% |
| DNA content (pg/ml) | <7000 | <30 | <30 |
| Virus recovered (*) (ELISA protein E) | 90% | 76% | 20% |

(*) Stepwise yields

The purified inactivated viral solution was used to immunize mice by injection on day 0 and then on day 7. The test with the virulent virus is carried out using a solution containing $10^5$ LD 50/ml on day 30. All the mice vaccinated with the purified undiluted preparation and with the purified preparation diluted to 1/32 were protected. In the same test, the mice vaccinated with Biken vaccine (1/32 dilution) were tested and only 2/5 of them were protected.

What is claimed is:

1. A process for the industrial production of a vaccine against Japanese encephalitis, comprising:

a) culturing cells from a cell line on a cell culture medium, b) inoculating the cells with Japanese encephalitis virus in the presence of a viral multiplication medium, c) propagating and multiplying the virus, d) harvesting the viral multiplication medium, e) purifying viruses from the viral multiplication medium by at least one ion-exchange chromatographic step, followed by adsorption chromatography and gel permeation, and f) formulating and incorporating the viruses from the viral multiplication medium in a pharmaceutical form.

2. The process according to claim 1, wherein the amount of virus inoculated corresponds to a multiplicity of infection (MOI) of less than 0.1.

3. The process according to claim 1, further comprising inactivating the viruses harvested from the viral multiplication medium before or after purification.

4. The process according to claim 3, wherein the inactivation is performed using a chemical agent at room temperature.

5. The process according to claim 1, wherein the cells are Vero cells.

6. The process according to claim 1, further comprising reintroducing new viral multiplication medium after the harvesting and repeating c)–f).

7. The process according to claim 6, wherein the reintroducing of the new viral multiplication medium and subsequent repeating of c)–f) is performed 2, 3, 4, 5, or 6 times.

8. The process according to claim 1, further comprising filtering the viral multiplication medium after the harvesting and before the purifying.

9. The process according to claim 1, wherein the viral multiplication medium possesses a protein concentration of less than 5 g/l.

10. A vaccine against Japanese encephalitis obtained by the method of claim 1, wherein the cellular DNA content of the vaccine is less than 100 pg/dose.

* * * * *